United States Patent [19]

Berneth et al.

[11] 4,426,530
[45] Jan. 17, 1984

[54] TRIAZOLYLCOUMARIN COMPOUNDS, AND THEIR PREPARATION AND USE AS OPTICAL BRIGHTENERS, SCINTILLATORS AND LASER DYESTUFFS

[75] Inventors: Horst Berneth, Odenthal-Gloebusch; Roderich Raue, Leverkusen, both of Fed. Rep. of Germany

[73] Assignee: Bayer Aktiengesellschaft, Leverkusen, Fed. Rep. of Germany

[21] Appl. No.: 335,987

[22] Filed: Dec. 30, 1981

[30] Foreign Application Priority Data

Jan. 16, 1981 [DE] Fed. Rep. of Germany ....... 3101141

[51] Int. Cl.³ .................. C07D 406/14; C09K 9/02; C09K 11/06
[52] U.S. Cl. ........................... 548/256; 252/301.29; 548/255; 548/262; 542/417; 542/419
[58] Field of Search ................ 548/256; 252/301.29

[56] References Cited

U.S. PATENT DOCUMENTS

| | | | |
|---|---|---|---|
| 3,271,412 | 9/1966 | Raue et al. | 548/256 |
| 3,839,351 | 10/1974 | Dorlars et al. | 548/256 |
| 3,925,405 | 12/1975 | Boehmke et al. | 548/256 |
| 4,005,098 | 1/1977 | Dorlars et al. | 548/256 |
| 4,120,864 | 10/1978 | Seidel et al. | 548/262 |
| 4,284,787 | 8/1981 | Knupfer et al. | 548/256 |

FOREIGN PATENT DOCUMENTS

| | | |
|---|---|---|
| 21304 | 1/1981 | European Pat. Off. . |
| 2006253 | 5/1979 | United Kingdom . |

OTHER PUBLICATIONS

Papini et al., Chemical Abstracts, Cols. 966–967 (1956).

*Primary Examiner*—Alton D. Rollins
*Attorney, Agent, or Firm*—Sprung, Horn, Kramer & Woods

[57] ABSTRACT

Optical brighteners of the formula

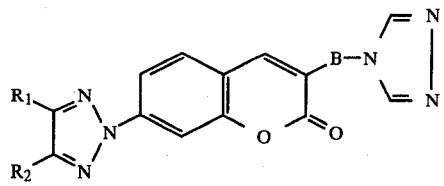

wherein
  B denotes a direct bond or the 1,4-phenylene radical and
  $R_1$ and $R_2$ independently of one another denote hydrogen, optionally substituted alkyl, aralkyl, cycloalkyl or aryl, or together form a fused aromatic ring, or the quaternisation products and protonation products thereof, are outstandingly suitable for the white tinting of polyester fibres or acrylic fibres. They are distinguished by a good build-up capacity and a small tendency to develop a green tone.

3 Claims, No Drawings

TRIAZOLYLCOUMARIN COMPOUNDS, AND THEIR PREPARATION AND USE AS OPTICAL BRIGHTENERS, SCINTILLATORS AND LASER DYESTUFFS

The invention relates to triazolylcoumarins of the formula

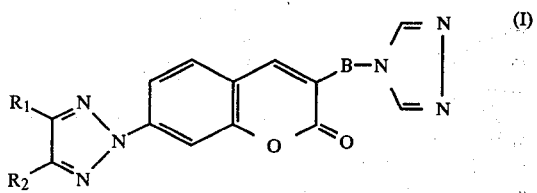

wherein
- B denotes a direct bond or the 1,4-phenylene radical and
- $R_1$ and $R_2$ independently of one another denote hydrogen, optionally substituted alkyl, aralkyl, cycloalkyl or aryl, or together form a fused aromatic ring, and the quaternisation products and protonation products thereof.

Alkyl radicals which have 1-4 C atoms and which are unsubstituted and straight-chain are especially suitable alkyl radicals.

Phenyl radicals which are mono-substituted to tri-substituted by Cl, phenyl, $C_1$-$C_4$-alkyl or $C_1$-$C_4$-alkoxy are suitable aryl radicals.

Benzyl and phenylethyl are suitable aralkyl radicals.
Cyclohexyl radicals are suitable cycloalkyl radicals.

Suitable quaternisation products and protonation products are those which are obtained from the "neutral" compounds of the formula I by treatment with quaternisation agents and protonation agents which are customary in dyestuff chemistry or brightener chemistry, such as those described, for example, in DE-OS (German Published Specification) No. 2,821,116 or U.S. Pat. No. 4,051,117.

Dimethyl sulphate, diethyl sulphate, hydrochloric acid, optionally Cl-substituted or $CH_3$-substituted benzenesulphonic acid, formic acid, acetic acid and lactic acid are preferred agents of this type.

Preferred compounds according to the invention are those of the formula I wherein
- $R_1$ denotes $C_1$-$C_4$-alkyl,
- $R_2$ denotes $C_1$-$C_4$-alkyl or phenyl which is optionally substituted by phenyl, $CH_3$, $OCH_3$ or Cl, or
- $R_1$ and $R_2$ together form a fused benzene ring or naphthalene ring.

Compounds of the formula I
wherein
- $R_1$ denotes methyl,
- $R_2$ denotes ethyl, phenyl or 4-biphenylyl, or
- $R_1$ and $R_2$ together form the missing members of a naphthalene ring linked via $C_1$/$C_2$, are particularly preferred.

The new triazolylcoumarins are accessible by various processes.

One process is characterised in that salicylaidehydes of the formula

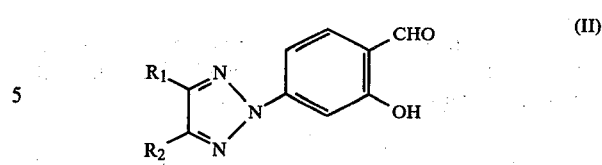

are condensed, in a manner which is in itself known (see U.S. Pat. No. 3,271,412 or German Patent Specification No. 1,296,121), with triazole compounds of the formula

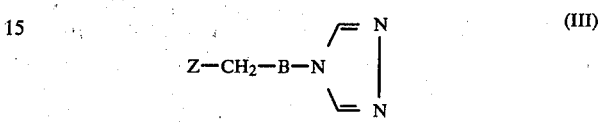

or the quaternisation products or protonation products thereof, wherein
- Z is an optionally functionally changed carboxyl group.

COOH, $COOC_nH_{2n+1}$ ($n=1-4$) and CN are suitable radicals Z.

The compounds of the formula II are virtually all known (see DE-OS (German Published Specification) 2,335,218 and DE-OS (German Published Specification) No. 2,848,670).

The "neutral" compounds of the formula III have also been described in the literature (see U.S. Pat. No. 4,120,864).

When B denotes a direct bond, the "neutral" compounds of the formula III are also obtainable by the reaction of 1,2,4-triazoles of the formula

wherein
- R' denotes a tri-($C_1$-$C_4$-alkyl)-silyl group, a $C_1$-$C_6$-alkanoyl group, a benzoyl group, a $C_1$-$C_6$-alkylsulphonyl group, a phenylsulphonyl group, a $C_1$-$C_6$-alkoxycarbonyl group, a phenoxycarbonyl group, a $C_1$-$C_6$-alkylaminocarbonyl group, a phenylaminocarbonyl group, a $C_1$-$C_6$-alkylaminothiocarbonyl group or a phenylaminothiocarbonyl group in which the phenyl radical can also carry methyl, methoxy, chlorine and/or hydroxycarbonyl, preferably with halogenoacetic acid derivatives of the formula

Z—$CH_2$—Hal (V)

wherein
- Hal is chlorine, bromine or iodine and
- Z is an optionally functionally changed carboxyl group.

When B denotes a direct bond, the quaternisation products of the compounds of the formula III can also be prepared by the reaction of 1,2,4-triazoles of the formula IV, wherein R' denotes the quaternisation group, preferably with halogenoacetic acid derivatives of the formula V, in addition to the possible preparation by quaternisation of the appropriate neutral compounds.

A further process for the preparation of the compounds of the formula I is characterised in that aminocoumarins of the formula

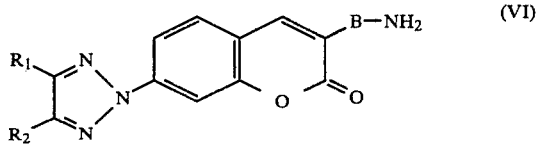

are reacted, also in a manner which is in itself known (see U.S. Pat. No. 4,120,864 and J. Chem. Soc. 1967, 1664–1666), with amidrazones of the formula

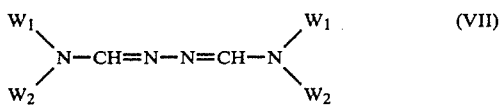

wherein $W_1$ and $W_2$ denote $C_1$-$C_4$-alkyl or phenyl, or together denote —$(CH_2)_4$— or —$(CH_2)_5$—, and the reaction products are then quaternised or protonated, if appropriate.

The reaction of VI with VII is preferably effected in a customary polar organic solvent at reflux temperatures of the solvent and, if appropriate, in the presence of an acid or basic catalyst.

The compounds of the formula VII are described in the abovementioned literature.

The aminocoumarins VI are either known from J. Ind. Chem. Soc. 48, 371 (1971) and U.S. Pat. No. 2,702,296 or are obtainable by analogous processes.

Furthermore, the new coumarins of the formula I are obtained by the reaction of amidinocoumarins of the formula

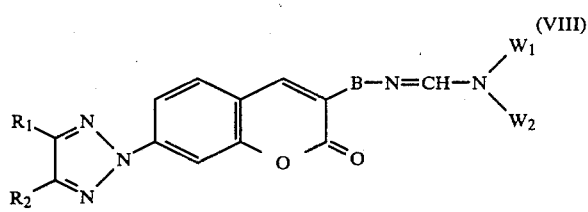

with formylhydrazine and, if appropriate, subsequent quaternisation or protonation.

The compounds of the formula VIII are obtained by the reaction of aminocoumarins of the formula VI, or the N-acylation products thereof, with Vilsmeyer compounds of the formula

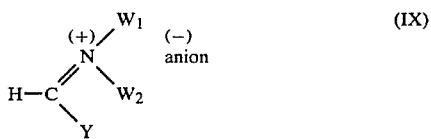

wherein Y denotes a leaving group, preferably halogen.

The reaction of the amidinocoumarins (VIII) is effected under conditions similar to those in the reaction of VI with VII.

Finally, the compounds of the formula I can be prepared by introducing, in a manner which is in itself known, the 1,2,3-triazol-2-yl radical at the 7-position of the coumarins of the formula

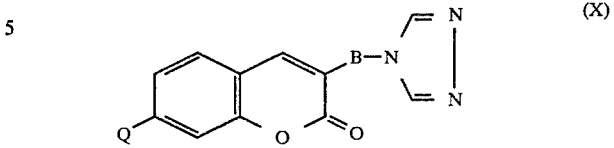

wherein Q represents $NH_2$ or $NH-NH_2$ (see U.S. Pat. No. 3,646,052 and DE-OS (German Published Specification) No. 1,670,914 = U.S. Pat. No. 3,666,758).

The reaction of appropriate 7-hydrazinocoumarins with suitable α-oximinoketones is preferred. The compounds of the formula X which are required as starting materials are obtained in a customary manner (see, for example, DE-OS (German Published Specification) No. 2,528,698) by reacting appropriate acylaminosalicylaldehydes with the compounds III, subsequently splitting off the acyl protective group and, if appropriate, converting the amino group into a hydrazino group (see DE-OS (German Published Specification) No. 2,528,698 = U.S. Pat. No. 4,069,228 and DE-OS (German Published Specification) No. 1 594 845 = U.S. Pat. No. 3,646,052).

The new coumarin compounds of the formula I, in a dissolved or finely divided state, exhibit a strong fluorescence and are outstandingly suitable as scintillators, laser dyestuffs and, preferably, as optical brighteners. Whilst the "neutral" compounds are preferably employed for the white tinting of textile materials composed of hydrophobic fibres, particularly polyester fibres, the quaternised and protonated products are used for brightening acid-modified fibre materials, such as, for example, acrylic fibres, according to customary dyeing methods.

The new whiteners are distinguished in this process by a high tinctorial strength, a good build-up capacity and a slight tendency to develop a green tone, even for high active compound concentrations.

EXAMPLE 1

6.50 g (20 mmols) of 3-(dimethylaminomethyleneamino)-7-(4-ethyl-5-methyl-2H-1,2,3-triazol-2-yl)-coumarin and 1.44 g (24.0 mmols) of formylhydrazine are refluxed in 18 ml of anhydrous dimethylformamide for 1.5 hours, under an $N_2$ atmosphere. After the mixture has been cooled, the thick yellow slurry is rapidly filtered off under suction, washed with 10 ml of anhydrous dimethylformamide and 20 ml of chloroform, and dried: 2.00 g (31%) of a pale yellow powder, which is recrystallized from dimethylacetamide: 1.62 g (25%) of 3-(1,2,4-triazol-4-yl)-7-(4-ethyl-5-methyl-2H-1,2,3-triazol-2-yl)-coumarin in the form of small pale yellow matted needles of melting point 263–264° C.

IR (KBr): 3110, 1740, 1618 cm$^{-1}$.

UV (dimethylformamide): $\tau_{max}$ (log ϵ) = 347 nm (4.518). Fluorescence: reddish-tinged blue.

The starting materials can be prepared by the following route:

50.6 g (200 mmols) of the Na salt of 2-hydroxy-4-(4-ethyl-5-methyl-2H-1,2,3-triazol-2-yl)-benzaldehyde, 6.00 g (80.0 mmols) of anhydrous sodium acetate, 18.0 g (240 mmols) of aminoacetic acid and 102 g (1.00 mol) of acetic anhydride are brought to reflux, during the course of 1 hour, under an $N_2$ atmosphere, and are boiled under reflux for 15 hours. After the mixture has been cooled to 90° C., 100 ml of methanol are added to it, and the mixture is refluxed for 30 minutes, cooled to 0° C. and filtered, and the residue is washed with 350 ml of methanol and dried: 55.3 g (89%) of a brown powder, which is recrystallised from 1,2-dichlorobenzene: 19.6 g (31%) of 3-acetylamino-7-(4-ethyl-5-methyl-2H-1,2,3-triazol-2-yl)-coumarin in the form of pink flakes of melting point 237°–238° C.

15.6 g (50.0 mmols) of 3-acetylamino-7-(4-ethyl-5-methyl-2H-1,2,3-triazol-2-yl)-coumarin are suspended in 100 ml of anhydrous dimethylformamide. 11.5 g (75.0 mmols) of phosphorus oxychloride are added dropwise to the suspension at 10°–15° C., and the mixture is stirred for 22 hours at room temperature. The slurry is introduced into 500 ml of ice water, and the mixture is filtered and brought to a pH of 8 with sodium carbonate. The yellow crystals are filtered off under suction, washed with water and dried: 15.5 g (95.5%). Recrystallisation from ethanol yields 12.9 g (80%) of 3-(dimethylaminomethyleneamino)-7-(4-ethyl-5-methyl-2H-1,2,3-triazol-2-yl)-coumarin in the form of small pale yellow crystals of melting point 158°–159° C.

IR (KBr): 1723, 1620 cm$^{-1}$.

UV (dimethylformamide): $\tau_{max}$ (log $\epsilon$)=280 (3.975), 370 nm (4.615).

The compounds of Examples 2–8 can be obtained in an analogous manner by this route. In Examples 5–8, the aminoacetic acid has to be replaced by 4-aminophenylacetic acid.

| Example | R$^1$ | R$^2$ | B | Fluorescence |
|---|---|---|---|---|
| 2 | CH$_3$ | C$_6$H$_5$ | — | blue |
| 3 | C$_2$H$_5$ | ![biphenyl] | — | blue |
| 4 | | ![naphthyl] | — | greenish-tinged blue |
| 5 | CH$_3$ | C$_2$H$_5$ | ![phenyl] | blue |

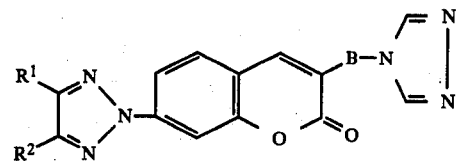

| Example | R$^1$ | R$^2$ | B | Fluorescence |
|---|---|---|---|---|
| 6 | CH$_3$ | C$_6$H$_5$ | ![phenyl] | greenish-tinged blue |
| 7 | C$_2$H$_5$ | ![biphenyl] | ![phenyl] | greenish-tinged blue |
| 8 | | ![naphthyl] | ![phenyl] | greenish-tinged blue |

EXAMPLE 9

15.0 g (50.0 mmols) of the Na salt of 2-hydroxy-4-(4-methyl-5-phenyl-2H-1,2,3-triazol-2-yl)-benzaldehyde, 7.75 g (50.0 mmols) of ethyl 1,2,4-triazol-4-yl-acetate, 1.50 g (25.0 mmols) of glacial acetic acid and 500 mg (6.00 mmols) of piperidine are refluxed in 70 ml of anhydrous ethanol for 8 hours under an N$_2$ atmosphere. The mixture is rapidly filtered off under suction and the residue is washed with ethanol and water. Finally, the residue is again stirred with 100 ml of ethanol for 2 hours at 60° C., and the mixture is filtered off under suction and the residue is dried: 12.0 g (65%) of a pale yellow crystalline powder. Recrystallisation from dimethylformamide yields 9.64 g (52%) of 3-(1,2,4-triazol-4-yl)-7-(4-methyl-5-phenyl-2H-1,2,3-triazol-2-yl)-coumarin in the form of pale yellow microplatelets of melting point 324°–326° C. (decomposition).

IR (KBr): 3110, 1745, 1733, 1618 cm$^{-1}$.

UV (dimethylformamide): $\tau_{max}$ (log $\epsilon$)=355 nm (4.617).

Fluorescence: blue.

The compound is identical with that of Example 2.

The compounds of Examples 10–16 can be prepared in an analogous manner by this route. Instead of ethyl 1,2,4-triazol-4-yl-acetate, the esters of other alcohols, such as the methyl ester, propyl ester, butyl ester or benzyl ester, can also be used. In Examples 13–16, an ester of 4-(1,2,4-triazol-4-yl)-phenylacetic acid, for example the ethyl ester, is to be used instead.

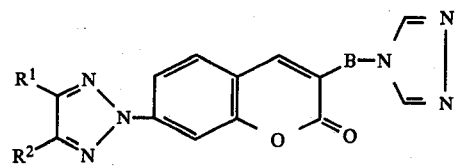

| Example | R$^1$ | R$^2$ | B | Fluorescence | Identical with Example |
|---|---|---|---|---|---|
| 10 | CH$_3$ | C$_2$H$_5$ | — | reddish-tinged blue | 1 |
| 11 | C$_2$H$_5$ | ![biphenyl] | — | blue | 3 |

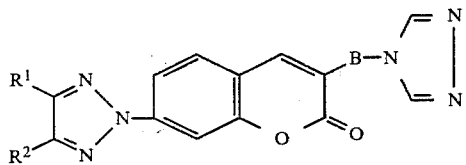

| Example | R¹ | R² | B | Fluorescence | Identical with Example |
|---|---|---|---|---|---|
| 12 | ![o-methylstyryl] | | — | greenish-tinged blue | 4 |
| 13 | CH₃ | C₂H₅ | ![phenylene] | blue | 5 |
| 14 | CH₃ | C₆H₅ | ![phenylene] | greenish-tinged blue | 6 |
| 15 | C₂H₅ | ![biphenyl] | ![phenylene] | greenish-tinged blue | 7 |
| 16 | ![o-methylstyryl] | | ![phenylene] | greenish-tinged blue | 8 |

EXAMPLE 17

17.3 g (50.0 mmols) of 3-(4-aminophenyl)-7-(4-ethyl-5-methyl-2H-1,2,3-triazol-2-yl)-coumarin, 10.5 g (75.0 mmols) of 1,2-bis-(dimethylaminomethylene)-hydrazine and 200 mg of 4-methylbenzenesulphonic acid are refluxed in 40 ml of anhydrous dimethylformamide for 10 hours under an N₂ atmosphere. A further 3.50 g (25.0 mmols) of 1,2-bis-(dimethylaminomethylene)-hydrazine are then added, and the mixture is refluxed for a further 10 hours. 16.1 g (81%) of pale yellow crystals are precipitated on cooling the mixture. Recrystallisation from dimethylformamide yields 14.3 g (72%) of 3-(4-(1,2,4-triazol-4-yl)-phenyl)-7-(4-ethyl-5-methyl-2H-1,2,3-triazol-2-yl)-coumarin in the form of small pale yellow crystals of melting point 321°–323° C.

IR (KBr): 3110, 1730, 1615, 1532 cm⁻¹.

UV (dimethylformamide): τ$_{max}$ (log ε)=357 nm (4.611).

¹H-NMR ([D₆]DMSO): τ=1.24 (t, J=7.5 Hz; 3H, C$\underline{H}_3$CH₂), 2.30 (s; 3H, CH₃), 2.67 (q, J=7.5 Hz; 2H; CH₃C$\underline{H}_2$) 7.84 (mc; 7H), 8.31

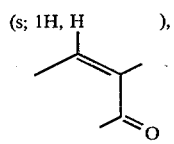

(s; 1H, H ), 9.13 (s; 2H, triazole).
Fluorescence: blue

The compound is identical with that of Examples 5 and 13.

The starting materials can be prepared by the following route:

50.6 g (200 mmols) of the Na salt of 2-hydroxy-4-(4-ethyl-5-methyl-2H-1,2,3-triazol-2-yl)-benzaldehyde, 41.8 g (200 mmols) of ethyl 4-nitrophenylacetate and 2 ml of piperidine are refluxed in 250 ml of ethanol for 4 hours. After the mixture has been cooled, it is neutralised with glacial acetic acid, and the residue is washed with ethanol and water, and dried: 46.3 g (61.5%). Recrystallisation from toluene yields 41.4 g (55%) of 3-(4-nitrophenyl)-7-(4-ethyl-5-methyl-2H-1,2,3-triazol-2-yl)-coumarin in the form of a pale yellow crystalline powder of melting point 278°–279° C.

IR (KBr): 1723, 1618, 1516, 1350 cm⁻¹.

37.6 g (100 mmols) of 3-(4-nitrophenyl)-7-(4-ethyl-5-methyl-2H-1,2,3-triazol-2-yl)-coumarin are suspended in 1,000 ml of ethanol. A solution of 160 g (708 mmols) of tin(II) chloride in 125 ml of concentrated hydrochloric acid is added dropwise to the suspension at the boiling point, during the course of 1.5 hours, and the mixture is refluxed for a further 3 hours. After the mixture has been cooled, it is filtered under suction, the residue is washed with ethanol and the filter cake is deprotonated by stirring it with 30 g of potassium carbonate in 600 ml of water and 600 ml of chloroform. The chloroform phase is evaporated after it has been dried over potassium carbonate, and the residue is recrystallised from toluene: 29.5 g (85%) of 3-(4-aminophenyl)-7-(4-ethyl-5-methyl-2H-1,2,3-triazol-2-yl)-coumarin in the form of a pale yellow powder of melting point 162°–163° C.

IR (KBr): 3465, 3375, 1723, 1620 cm$^{-1}$.

UV (dimethylformamide): $\tau_{max}$ (log $\epsilon$)=306 (4.204), 392 nm (4.453).

The compounds of Examples 18–20 can be prepared in an analogous manner by this route.

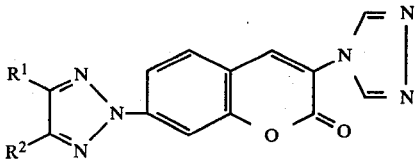

| Example | R$^1$ | R$^2$ | Fluorescence | Identical with Example |
|---|---|---|---|---|
| 18 | CH$_3$ | C$_6$H$_5$ | greenish-tinged blue | 6, 14 |
| 19 | C$_2$H$_5$ | –⟨O⟩–⟨O⟩ | greenish-tinged blue | 7, 15 |
| 20 | | ⟨naphthyl⟩ | greenish-tinged blue | 8, 16 |

EXAMPLE 21

3.48 g (22.0 mmols) of 1-methyl-4-cyanomethyl-1,2,4-triazolium chloride are added to 6.02 g (20.0 mmols) of the Na salt of 2-hydroxy-4-(4-methyl-5-phenyl-2H-1,2,3-triazol-2-yl)-benzaldehyde and 4.80 g (80.0 mmols) of glacial acetic acid in 20 ml of anhydrous dimethylformamide, under an N$_2$ atmosphere, and the mixture is stirred for 24 hours at room temperature. The precipitate is filtered off under suction, washed with dimethylformamide and dried: 3.60 g (43%) of a pale yellow powder. Recrystallisation from water yields 2.90 g (35%) of 1-methyl-4-[7-(4-methyl-5-phenyl-2H-1,2,3-triazol-2-yl)-coumarin-3-yl]-1,2,4-triazolium chloride in the form of small pale yellow crystals of melting point 249°–252° C. (decomposition).

IR (KBr): 3060, 1737, 1620 cm$^{-1}$.

UV (dimethylformamide): $\tau_{max}$ (log $\epsilon$)=360 nm (4.577).

Fluorescence: blue.

The reaction can also be carried out, in an analogous manner, using, for example, 1-methyl-4-(methylcarbonylmethyl)-1,2,4-triazolium chloride or 1-methyl-4-(ethoxycarbonylmethyl)-1,2,4-triazolium chloride.

The starting materials can be prepared by the following route:

16.6 g (200 mmols) of 1-methyl-1,2,4-triazole and 15.1 g (200 mmols) of chloroacetonitrile are warmed to 80° C. for 24 hours. On cooling, the melt immediately crystallises through: 31.7 g (100%) of colourless needles. Recrystallisation from ethanol/water yields 28.8 g (91%) of 1-methyl-4-cyano-methyl-1,2,4-triazolium chloride in the form of colourless needles of melting point 186°–187° C.

IR (KBr): 3170, 2255, 1820, 1583 cm$^{-1}$.

1-Ethyl-, 1-benzyl-, 1-(2-hydroxyethyl)- or 1-phenyl-1,2,4-triazole, for example, can also be reacted analogously with bromoacetic acid, methyl chloroacetate or ethyl bormoacetate, for example.

The compounds of Examples 22–27 can be prepared in an analogous manner by this route.

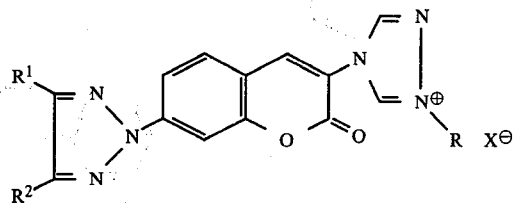

| Example | R$^1$ | R$^2$ | R | X | Fluorescence |
|---|---|---|---|---|---|
| 22 | CH$_3$ | C$_2$H$_5$ | CH$_3$ | Br | reddish-tinged blue |
| 23 | CH$_3$ | C$_6$H$_5$ | C$_2$H$_5$ | Cl | blue |
| 24 | C$_2$H$_5$ | –⟨O⟩–⟨O⟩ | –CH$_2$–⟨O⟩ | Br | blue |
| 25 | | ⟨naphthyl⟩ | –CH$_2$CH$_2$OH | Cl | greenish-tinged blue |
| 26 | CH$_3$ | C$_2$H$_5$ | –CH$_2$COOH | Cl | blue |
| 27 | C$_2$H$_5$ | C$_6$H$_5$ | C$_6$H$_5$ | Cl | greenish-tinged blue |

EXAMPLE 28

2.77 g (22.0 mmols) of dimethyl sulphate are added to 7.96 g (20.0 mmols) of 3-(4-(1,2,4-triazol-4-yl)-phenyl)-7-(4-ethyl-5-methyl-2H-1,2,3-triazol-2-yl)-coumarin in 45 ml of anhydrous dimethylformamide at 100° C., under an N$_2$ atmosphere. A solution is formed and is cooled, and toluene is added until the precipitation is complete: 8.16 g (78%) of 1-methyl-4-[4-(7-(4-ethyl-5-methyl-2H-1,2,3-triazol-2-yl)-coumarin-3-yl)- phenyl]1,2,4-triazolium methosulphate in the form of small pale yellow crystals of melting point 221°-225° C. (decomposition).

The compounds of Examples 29-35 can be prepared in an analogous manner by this route (in Examples 31 and 33, substituted alkyl halides are used).

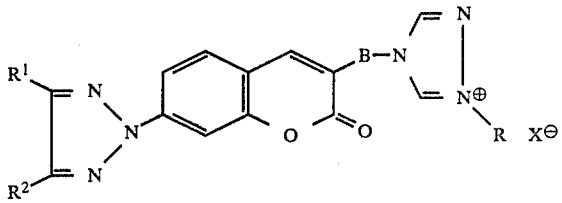

| Example | R¹ | R² | B | R | X | Fluorescence |
|---|---|---|---|---|---|---|
| 29 | $CH_3$ | $C_2H_5$ | — | $CH_3$ | $CH_3OSO_3$ | reddish-tinged blue |
| 30 | $CH_3$ | $C_6H_5$ | — | $C_6H_5$ | $C_2H_5OSO_3$ | blue |
| 31 | $C_2H_5$ | -biphenyl- | — | $C_3H_7$ | Br | blue |
| 32 |  | -o-tolyl-CH= | — | $CH_3$ | $CH_3OSO_3$ | greenish-tinged blue |
| 33 | $CH_3$ | $C_6H_5$ | -phenylene- | Benzyl | Br | greenish-tinged blue |
| 34 | $C_2H_5$ | -biphenyl- | -phenylene- | $CH_3$ | $CH_3OSO_3$ | greenish-tinged blue |
| 35 | -o-tolyl-CH= |  |  | -phenylene-$CH_2$-phenylene- | $-phenylene-CH_2OSO_3$ | greenish-tinged blue |

IR (KBr): 1724, 1620 cm$^{-1}$.

UV (dimethylformamide): $\tau_{max}$ (log $\epsilon$)=356 nm (4.607).

¹H-NMR ([D₆] DMSO): δ=1.26 (t, J=7.5 Hz; 3H, C$\underline{H_3}$CH₂), 2.33 (s, 3H, CH₃), 2.73 (q, J=7.5 Hz; 2H, CH₃C$\underline{H_2}$), 3.42 (s, 3H, CH₃OSO₃), 4.21 (s; 3H, CH₃N⊕), 7.8–8.15 (m; 7H), 8.45

(s; 1H, H 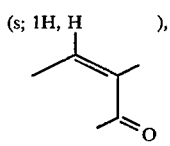 ), 9.83 (s; 1H, triazole), 10.85 (s; 1H, triazole).

Fluorescence: blue.

EXAMPLE 36

3.70 g (10.0 mmols) of 3-(1,2,4-triazol-4-yl)-7-(4-methyl-5-phenyl-2H-1,2,3-triazol-2-yl)-coumarin and 3.45 g (20.0 mmols) of methylbenzenesulphonate in 25 ml of anhydrous 1,2-dichlorobenzene are heated to 190° C. for 10 minutes. The suspension is filtered off under suction after cooling, and the residue is washed with 5 ml of hot 1,2-dichlorobenzene, and dried: 5.42 g (100%) of 1-methyl-4-[7-(4-methyl-5-phenyl-2H-1,2,3-triazol-2-yl)-coumarin-3-yl]-1,2,4-triazolium benzenesulphonate in the form of a pale yellow powder of melting point 261°-262° (decomposition).

IR (KBr): 3060, 1737, 1620 cm$^{-1}$.

UV (dimethylformamide): $\tau_{max}$ (log $\epsilon$)=360 nm (4.577).

Fluorescence: blue.

The compounds of Examples 37–43 can be prepared in an analogous manner by this route.

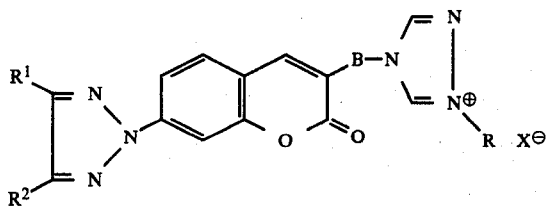

| Example | R¹ | R² | B | R | X | Fluorescence |
|---|---|---|---|---|---|---|
| 37 | $CH_3$ | $C_2H_5$ | — | $-CH_2-C_6H_5$ | $C_6H_5-SO_3$ | reddish-tinged blue |
| 38 | $C_2H_5$ | biphenyl | — | $CH_3$ | $CH_3SO_3$ | blue |
| 39 | o-methyl-styryl | | — | $C_2H_5$ | $CH_3-C_6H_4-SO_3$ | greenish-tinged blue |
| 40 | $CH_3$ | $C_2H_5$ | $-C_6H_4-$ | $CH_3$ | $CH_3SO_3$ | blue |
| 41 | $CH_3$ | $C_6H_5$ | $-C_6H_4-$ | $C_2H_5$ | $Cl-C_6H_4-SO_3$ | greenish-tinged blue |
| 42 | $C_2H_5$ | biphenyl | $-C_6H_4-$ | $CH_3$ | $C_6H_5-SO_3$ | greenish-tinged blue |
| 43 | o-methyl-styryl | | $-C_6H_4-$ | $CH_3$ | $CH_3SO_3$ | greenish-tinged blue |

EXAMPLE 44

6.44 g (20 mmols) of 3-(1,2,4-triazol-4-yl)-7-(4-ethyl-5-methyl-2H-1,2,3-triazol-2-yl)-coumarin are dissolved in 15 g of formic acid and 5 g of toluene at 50° C. Ethylene oxide is then introduced into the solution until a sample freed from toluene yields a clear solution in water. The toluene and the major part of the formic acid are then distilled off, in vacuo, from the complete mixture. 1-(2-Hydroxyethyl)-4-[7-(4-ethyl-5-methyl-2H-1,2,3-triazol-2-yl)-coumarin-3-yl]-1,2,4-triazolium formate and glycol formate remain, and these compounds can be taken up in water to give a 20–30% strength solution.

Fluorescence: reddish-tinged blue.

The compounds of Examples 45–52 can be prepared in an analogous manner by this route. In Example 52, acrylonitrile is added instead of ethylene oxide.

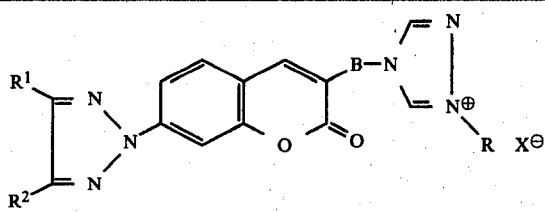

| Example | R¹ | R² | B | R | X | Fluorescence |
|---|---|---|---|---|---|---|
| 45 | $CH_3$ | $C_6H_5$ | — | $-CH_2CH_2OH$ | $CH_3COO$ | blue |

-continued

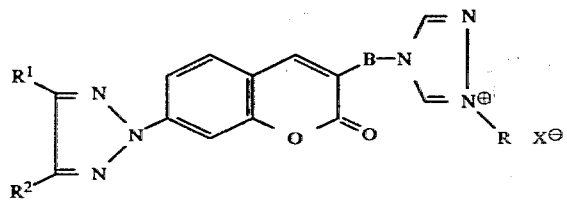

| Example | R¹ | R² | B | R | X | Fluorescence |
|---|---|---|---|---|---|---|
| 46 | C₂H₅ | | biphenyl-diyl | -CH(CH₃)-CH₂OH | HCOO | blue |
| 47 | | o-methylstyryl | — | -CH₂CH₂OH | CH₃CH(OH)COO | greenish-tinged blue |
| 48 | CH₃ | C₂H₅ | | phenylene | -CH₂CH₂OH | HCOO | blue |
| 49 | CH₃ | C₆H₅ | phenylene | -CH(CH₃)-CH₂OH | CH₃COO | greenish-tinged blue |
| 50 | C₂H₅ | | biphenyl-diyl | phenylene | -CH(CH₃)-CH₂OH | CH₃CH(OH)COO | greenish-tinged blue |
| 51 | | o-methylstyryl | phenylene | -CH₂CH₂OH | HCOO | greenish-tinged blue |
| 52 | CH₃ | C₆H₅ | — | -CH₂CH₂CN | HCOO | blue |

EXAMPLE 53

3.98 g (10.0 mmols) of 3-(4-(1,2,4-triazol-4-yl)-phenyl)-7-(4-ethyl-5-methyl-2H-1,2,3-triazol-2-yl)-coumarin in 15 ml of dimethylformamide are warmed to 70° C., and 70% strength perchloric acid is added to the mixture until a solution is formed. After the mixture has cooled, it is diluted with water, and the pale yellow precipitate is filtered off under suction and washed with water: 3.43 g (85%) of 4-[4-(7-(4-ethyl-5-methyl-2H-1,2,3-triazol-2-yl)-coumarin-3-yl)-phenyl]-1,2,4-triazolium perchlorate of melting point 260°–264° C. (decomposition).

Fluorescence: blue.

The compounds of Examples 54–60 can be prepared in an analogous manner by this route.

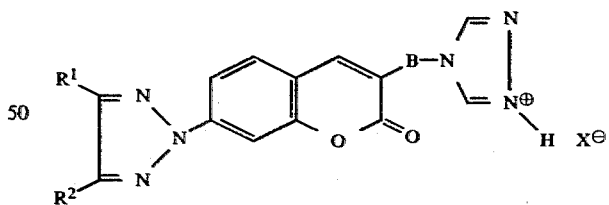

| Example | R¹ | R² | B | X | Fluorescence |
|---|---|---|---|---|---|
| 54 | CH₃ | C₂H₅ | — | BF₄ | reddish-tinged blue |
| 55 | CH₃ | C₆H₅ | — | Cl | blue |
| 56 | C₂H₅ | | biphenyl-diyl | — | Br | blue |
| 57 | | o-methylstyryl | — | ClO₄ | greenish-tinged blue |
| 58 | CH₃ | C₆H₅ | phenylene | Cl | greenish-tinged blue |

-continued

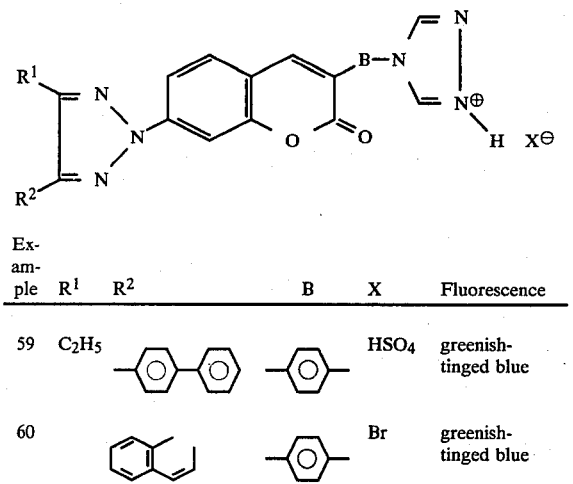

| Example | R¹ | R² | B | X | Fluorescence |
|---|---|---|---|---|---|
| 59 | C₂H₅ | -⟨O⟩-⟨O⟩- | -⟨O⟩- | HSO₄ | greenish-tinged blue |
| 60 | | (naphthyl) | -⟨O⟩- | Br | greenish-tinged blue |

EXAMPLE 61

Polyacrylonitrile textile fabrics are treated, in the liquor ratio of 1:40, by boiling for 30 minutes with a dye liquor which contains 0.2% of the compound of formula 21, 8% of sodium chlorite (50% strength), 4% of sodium nitrate and 4% of a chlorite stabiliser (all percentage data relative to the textile material), and the liquor is adjusted to pH 3.5 with formic acid. After the rinsing and drying processes, a polyacrylonitrile fabric which is very well and brilliantly brightened is obtained.

Similar results are obtained if the same procedure as described above is followed, but the compounds of the formulae 24, 26, 32, 33, 38 or 40 are employed.

We claim:

1. Triazolylcoumarins of the formula

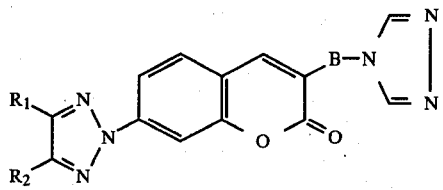

wherein

B denotes a direct bond or the 1,4-phenylene radical and $R_1$ denotes $C_1$–$C_4$-alkyl, $R_2$ denotes $C_1$–$C_4$-alkyl or phenyl which is optionally substituted by phenyl, $CH_3$, $OCH_3$ or Cl, as well as derivatives thereof obtained from these compounds by treatment with dimethyl sulphate, diethyl sulphate, hydrochloric acid, optionally Cl-substituted or $CH_3$-substituted benzenesulphonic acid, formic acid, acetic acid and lactic acid.

2. Coumarins of claim 1 wherein
$R_1$ denotes methyl and
$R_2$ denotes ethyl, phenyl or 4-biphenylyl.

3. Coumarins of claim 1 wherein
$R_1$ denotes methyl and
$R_2$ denotes phenyl.

* * * * *

UNITED STATES PATENT AND TRADEMARK OFFICE
CERTIFICATE OF CORRECTION

PATENT NO. : 4,426,530
DATED : January 17, 1984
INVENTOR(S) : Horst Berneth et al It is certified that error appears in the above-identified patent and that said Letters Patent is hereby corrected as shown below:

| | |
|---|---|
| Col. 1, line 67 | Delete "salicylaidehydes" and insert --salicylaldehydes-- |
| Col. 7, line 56 | After "DMSO):"delete "$\tau$" and insert --$\sigma$-- |
| Col. 9, line 11 | End of formula delete "  " and insert -- 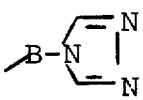 -- |
| Col. 12, 2nd line under "R" | Delete "$C_6H_5$" and insert --$C_2H_5$-- |
| Col. 12, line 40, under "R", last line | Delete "=$CH_2$-" and insert -- -$CH_2$- -- |
| Col. 11, line 57 | After "(s" delete "," and insert --;-- |
| Col. 11, line 58 | After "(s" delete "," and insert --;-- |

Signed and Sealed this

Eighth Day of October 1985

[SEAL]

Attest:

DONALD J. QUIGG

Attesting Officer

Commissioner of Patents and Trademarks—Designate